United States Patent
Saito

(10) Patent No.: US 8,825,125 B2
(45) Date of Patent: Sep. 2, 2014

(54) ENDOSCOPE SYSTEM AND PROCESSOR APPARATUS THEREOF, AND IMAGE GENERATING METHOD

(75) Inventor: Takaaki Saito, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 242 days.

(21) Appl. No.: 13/333,794

(22) Filed: Dec. 21, 2011

(65) Prior Publication Data

US 2012/0179013 A1    Jul. 12, 2012

(30) Foreign Application Priority Data

Jan. 12, 2011    (JP) ................. 2011-004195

(51) Int. Cl.
*A61B 5/1455*    (2006.01)

(52) U.S. Cl.
USPC ............................ 600/339; 600/310; 600/323

(58) Field of Classification Search
USPC ................................................ 600/310–344
See application file for complete search history.

(56) References Cited

U.S. PATENT DOCUMENTS

| | | |
|---|---|---|
| 5,512,940 A | 4/1996 | Takasugi et al. |
| 5,956,416 A | 9/1999 | Tsuruoka et al. |

FOREIGN PATENT DOCUMENTS

| | | |
|---|---|---|
| JP | 2648494 B2 | 8/1997 |
| JP | 2768936 B2 | 6/1998 |

OTHER PUBLICATIONS

European Search Report dated May 7, 2012.

*Primary Examiner* — Eric Winakur
*Assistant Examiner* — Marjan Fardanesh
(74) *Attorney, Agent, or Firm* — McGinn IP Law Group, PLLC

(57) ABSTRACT

An image of a target portion is captured while first light beams are applied thereto. Thereby, a first image signal is obtained. The first light beams are in a wavelength range in which an absorption coefficient varies in accordance with a change in oxygen saturation of hemoglobin in blood. An image of the target portion is captured while second light beams in a broadband wavelength range are applied thereto. Thereby, second and third image signals are obtained. Oxygen saturation is calculated from the first to third image signals. Reliability of the oxygen saturation is calculated from one of the first to third image signals. Color difference signals each corresponding to the oxygen saturation is obtained from a color table. Each of the color difference signals is corrected in accordance with the reliability. An oxygen saturation image is generated based on corrected color difference signals and displayed.

16 Claims, 14 Drawing Sheets

ENDOSCOPE SYSTEM AND PROCESSOR APPARATUS THEREOF, AND IMAGE GENERATING METHOD

BACKGROUND OF THE INVENTION

1. Field of the Invention

The present invention relates to an endoscope system for displaying information on oxygen saturation of hemoglobin in blood, a processor apparatus of an endoscope system, and an image generating method.

2. Description Related to the Prior Art

Recently, diagnoses using an endoscope have been performed commonly. In addition to normal observation of a portion of a subject using an endoscope apparatus with illumination of broadband light (white light), special observation using illumination of narrowband light has come into practice. By using the narrowband light, blood vessels in the portion being observed are highlighted in display.

Furthermore, functional information such as oxygen saturation of hemoglobin in blood and blood vessel depth is obtained from an image signal from an endoscope apparatus. The functional information is obtained based on light absorption property of blood vessels and scattering characteristic of living tissue. Then, an image representing the functional information is generated. For example, in Japanese Patent No. 2648494, colors are assigned according to different oxygen saturation levels. A pseudo-color oxygen saturation image is generated based on the colors assigned. Such oxygen saturation image facilitates finding, for example, a cancer causing a low-oxygen or hypoxic condition.

The oxygen saturation is obtained by performing image processing to an image signal. Reliability of the oxygen saturation declines when the image signal is obtained under inappropriate imaging conditions, for example, when a pixel value of the image signal is extremely high due to a large quantity of illumination light applied to the portion being observed.

To solve the problem, in Japanese Patent No. 2768936 and U.S. Pat. No. 5,956,416 (corresponding to Japanese Patent No. 3217343), a region in which a pixel value of an image signal exceeds a predetermined value is detected as an ineffective region. The ineffective region is subjected to processing (for example mask processing) to be displayed differently from an effective region in which the pixel value remains within a predetermined range. Thereby, it becomes easy for a user to distinguish a region with accurate functional information, such as the oxygen saturation, from a region with inaccurate functional information.

Because the ineffective region is clearly distinguished from the effective region in the Japanese Patent No. 2768936 and the U.S. Pat. No. 5,956,416, an appropriate threshold value for determining a boundary value between the effective and ineffective regions is important. When the threshold value is inappropriate, a region with accurate oxygen saturation may be determined as the ineffective region. Conversely, a region with inaccurate oxygen saturation may be determined as the effective region.

In addition to the intensity of the illumination light described in the Japanese Patent No. 2768936 and the U.S. Pat. No. 5,956,416, the following factors make the oxygen saturation inaccurate.

1. an artificial object captured in an image
2. dirt on mucosal surface (opaque mucosa or residue adhered to the mucosal surface)
3. different spectral distribution characteristics between spectral images in different wavelength ranges The Japanese Patent No. 2768936 and the U.S. Pat. No. 5,956,416 cannot detect abnormality in the oxygen saturation caused by the above factors.

SUMMARY OF THE INVENTION

An object of the present invention is to provide an endoscope system, a processor apparatus thereof, and an image generating method capable of displaying information on oxygen saturation with higher accuracy.

To achieve the above and other objects, the endoscope system of the present invention includes an illuminating section, an image signal obtaining section, an oxygen saturation calculator, a reliability calculator, an image processing section, and a display section. The illuminating section projects illumination light to a portion to be observed. The portion includes a blood vessel. The image signal obtaining section has an image sensor. The image signal obtaining section captures reflection light reflected from the portion using the image sensor to obtain at least first to third image signals. The first image signal is obtained from first reflection light including a wavelength range in which an absorption coefficient varies in accordance with oxygen saturation of hemoglobin in blood. The second image signal is obtained from second reflection light including a wavelength range in which an absorption coefficient varies in accordance with blood volume. The third image signal is a reference signal of the first and second image signals. The oxygen saturation calculator obtains oxygen saturation information on a picture element by picture element basis based on the first to third image signals. The reliability calculator determines reliability of the oxygen saturation information on the picture element by picture element basis relative to at least one of the first to third image signals. The image processing section generates an oxygen saturation image based on the oxygen saturation information and the reliability. The display section displays the oxygen saturation image.

It is preferable that the image processing section includes a color tone information memory and an oxygen saturation image generator. The color tone information memory stores a relation between the oxygen saturation information and color tone information. The oxygen saturation image generator corrects the color tone information with the reliability and generates the oxygen saturation image from corrected color tone information. The color tone information is read out from the color tone information memory based on the oxygen saturation information.

It is preferable that the reliability calculator determines the reliability in accordance with a pixel value of the picture element.

It is preferable that the reliability decreases gradually when the pixel value exceeds an upper limit or when the pixel value is less than a lower limit.

It is preferable that the reliability calculator determines the reliability based on a signal ratio between at least the two image signals and an optical absorption spectrum of the hemoglobin in blood.

It is preferable that the reliability calculator determines the reliability in accordance with a position of the picture element.

It is preferable that the reliability is the highest when the picture element is located at a central area of an image, and the reliability decreases as the picture element is located closer to a peripheral area of the image.

It is preferable that the color tone information is a signal value of a color difference signal.

It is preferable that the image sensor is a color image sensor provided with R, G, and B color filters on an imaging surface. It is preferable that white light is used as the illumination light to obtain the second and third image signals.

It is preferable that the white light is pseudo white light generated by applying excitation light of a predetermined wavelength to a phosphor.

A processor apparatus used with an endoscope includes an oxygen saturation calculator, a reliability calculator, and an image processing section. The oxygen saturation calculator obtains oxygen saturation information on a picture element by picture element basis based on the first to third image signals. The reliability calculator determines reliability of the oxygen saturation information on the picture element by picture element basis relative to at least one of the first to third image signals. The image processing section generates an oxygen saturation image based on the oxygen saturation information and the reliability.

An image generating method includes a projecting step, an obtaining step, an information obtaining step, a reliability determining step, and a generating step. In a projecting step, illumination light is projected to a portion to be observed. The portion includes a blood vessel. In the obtaining step, at least first to third image signals are obtained from reflection light reflected from the portion. The first image signal is obtained from first reflection light including a wavelength range in which an absorption coefficient varies in accordance with oxygen saturation of hemoglobin in blood. The second image signal is obtained from second reflection light including a wavelength range in which an absorption coefficient varies in accordance with blood volume. The third image signal is a reference signal of the first and second image signals. In the information obtaining step, oxygen saturation information is obtained on a picture element by picture element basis based on the first to third image signals. In the reliability determining step, reliability of the oxygen saturation information is determined on the picture element by picture element basis relative to at least one of the first to third image signals. In the generating step, an oxygen saturation image is generated based on the oxygen saturation information and the reliability.

According to the present invention, the color tone information, used for generating the oxygen saturation image, varies in accordance with the reliability of the oxygen saturation information. Accordingly, the oxygen saturation information is displayed with higher accuracy without distinguishing an ineffective region from an effective region. The reliability is determined based on a signal ratio related to the absorption spectrum of the hemoglobin in blood or a position of the picture element in an image signal, in addition to a pixel value of the image signal. Thereby, information related to abnormalities (dirt on mucosal surface, pigment, uneven light distribution, for example) are reflected on the reliability.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
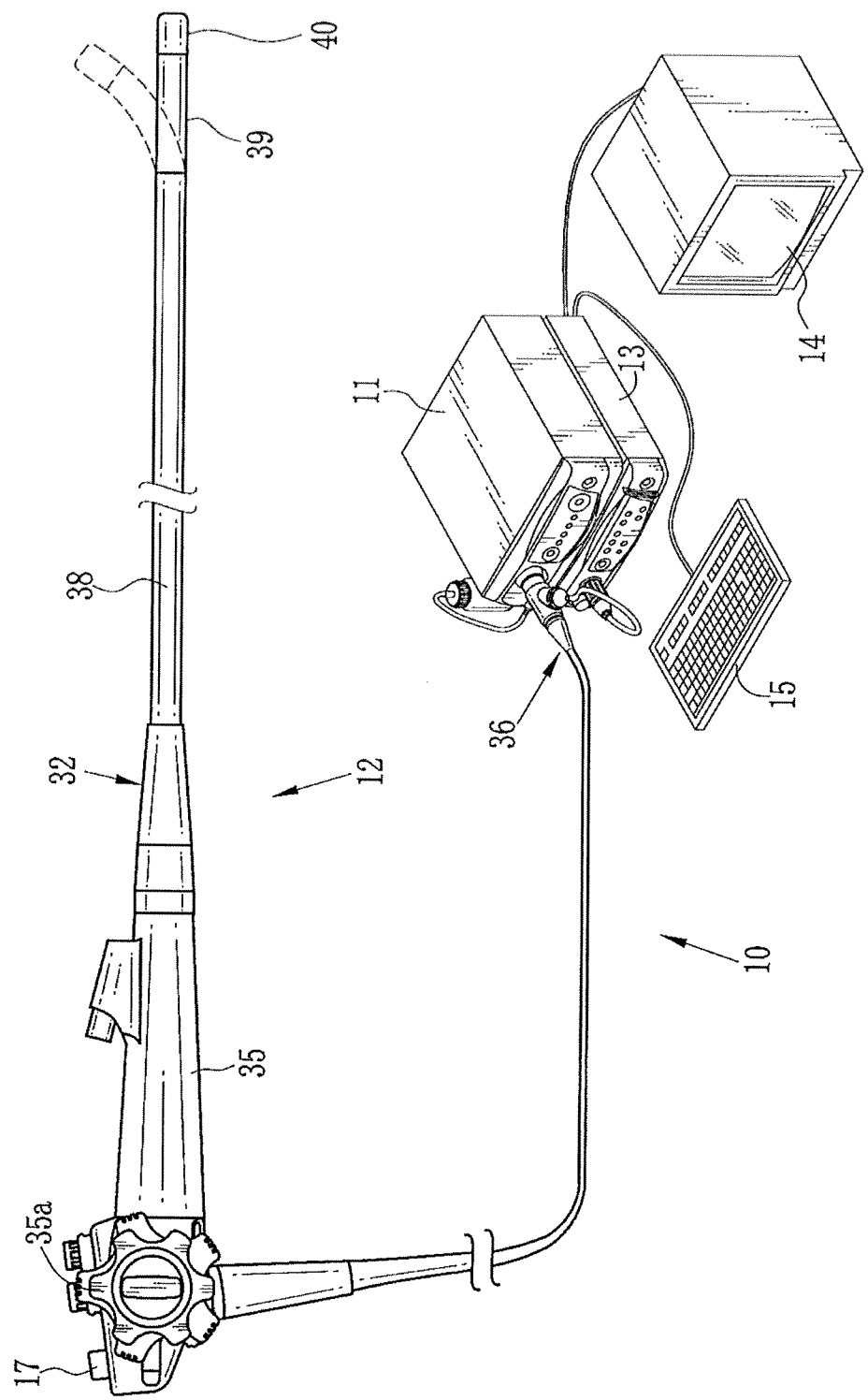
FIG. 1 is an external view of an endoscope system of a first embodiment.
Figure 2:
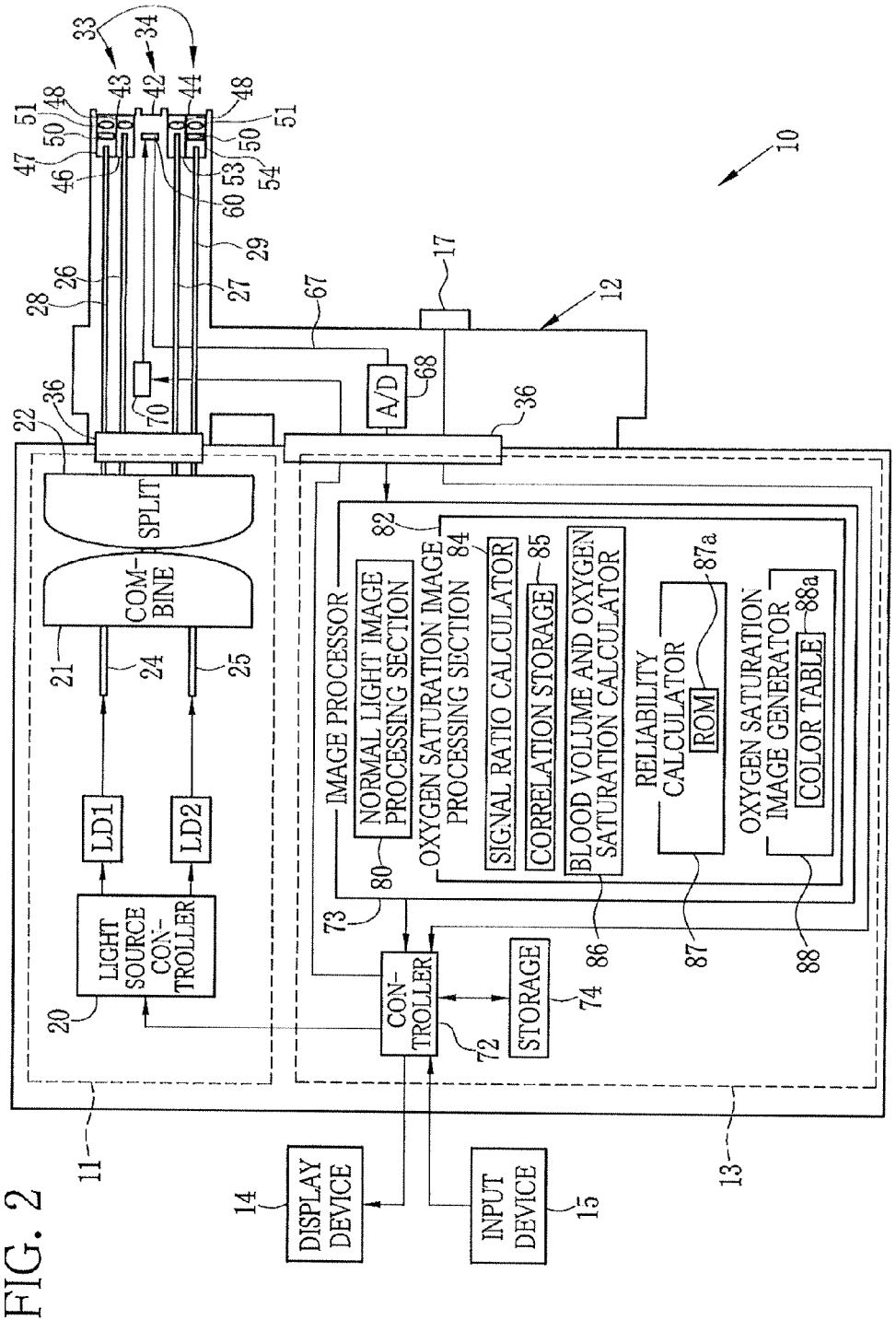
FIG. 2 is a block diagram showing a configuration of an endoscope system.

As shown in FIGS. 1 and 2, an endoscope system 10 of a first embodiment is provided with a light source apparatus 11, an endoscope apparatus 12, a processor apparatus 13, a display device 14, and an input device 15. The light source apparatus 11 generates light in a predetermined wavelength range. The endoscope apparatus 12 guides the light from the light source apparatus 11 and applies the light as illumination light to a portion to be observed (hereinafter may referred to as the target portion) of a subject. The endoscope apparatus 12 captures an image of light reflected from the target portion and the like. The processor apparatus 13 performs image processing to an image signal obtained with the endoscope apparatus 12. The display device 14 displays an endoscopic image and the like from the processor apparatus 13. The input device 15 includes a keyboard, for example.

The endoscope system 10 has two observation modes: a normal light mode and an oxygen saturation mode. In the normal light mode, a normal light image is displayed on the display device 14. The normal light image is a subject image of visible light in a wavelength range from blue to red. In the oxygen saturation mode, an oxygen saturation image is displayed on the display device 14. The oxygen saturation image is a pseudo color image showing information on oxygen saturation of hemoglobin in blood in blood vessel(s) included in the target portion. The observation mode is switched as necessary based on a command inputted from a selection switch 17 of the endoscope apparatus 12 or the input device 15, for example.

The light source apparatus 11 is provided with two kinds of laser light sources LD1 and LD2, a light source controller 20, a combiner 21, and a splitter 22. The laser light source LD1 generates narrowband light beams (oxygen saturation measuring beams) used for measuring the oxygen saturation. The laser light source LD2 applies excitation light beams to a phosphor 50, placed at the distal end of the endoscope apparatus 12, to generate white light (pseudo white light). The light beams from the laser light source LD1 are incident on an optical fiber 24 through a condenser lens (not shown). The light beams from the laser light source LD2 are incident on an optical fiber 25 through a condenser lens (not shown). For each of the laser light sources LD1 and LD2, a broad area InGaN laser diode, an InGaNAs laser diode, or a GaNAs laser diode can be used, for example.

The light source controller 20 controls the laser light sources LD1 and LD2 to adjust emission timing of each of the laser light sources LD1 and LD2 and a light quantity ratio between the laser light sources LD1 and LD2. In this embodiment, in the normal light mode, the laser light source LD1 is turned off and the laser light source LD2 is turned on. On the other hand, in the oxygen saturation mode, the laser light sources LD1 and the LD2 are turned on alternately at predetermined time intervals.

The combiner 21 combines the light beams from the optical fiber 24 and the light beams from the optical fiber 25. The splitter 22 splits the combined light beams into four paths. Out of the four paths of light beams, the light beams from the laser light source LD1 are transmitted through light guides 26 and 27. The light beams from the laser light source LD2 are transmitted through light guides 28 and 29. Each of the light guides 26 to 29 is composed of a bundle fiber that is a plurality of optical fibers bundled together. Note that the light beams from the laser light sources LD1 and LD2 may be directly incident on the light guides 26 to 29 without using the combiner 21 and the splitter 22.

The endoscope apparatus 12 is composed of an electronic endoscope and is provided with a scope 32, an illuminating section 33, an imaging section 34, an operation section 35, and a connector section 36. The illuminating section 33 applies the four paths of light beams transmitted through the respective light guides 26 to 29 to the target portion. The imaging section 34 captures an image of the target portion. The operation section 35 is used for bending an end portion of the scope 32 and performing the observation. The connector section 36 connects the scope 32, the light source apparatus 11, and the processor apparatus 13 in a detachable manner.

The scope 32 is provided with a flexible portion 38, a bending portion 39, and a distal portion 40 in this order from the operation section 35 side. The flexible portion 38 is flexible inside the subject when the scope 32 is inserted into the subject. The bending portion 39 is bent by rotating an angle knob 35a disposed in the operation section 35. The bending portion 39 can be bent at any angle in a vertical or horizontal direction to direct the distal portion 40 to the target portion.

The distal portion 40 is provided with the illuminating section 33 and the imaging section 34. The imaging section 34 is provided with a capture window 42 substantially at the center of the distal portion 40. The capture window 42 passes the light reflected from the target portion and the like. The illuminating section 33 includes two illumination windows 43 and 44 provided on respective sides of the imaging section 34. Each of the illumination windows 43 and 44 projects two types of light, the oxygen saturation measuring beams and the white light, to the target portion.

Two projection units 46 and 47 are disposed behind the illumination window 43. The projection unit 46 projects the oxygen saturation measuring beams from the light guide 26 to the target portion through a lens 48. The projection unit 47 applies the excitation light beams from the light guide 28 to the phosphor 50 to project white light. The white light is projected to the target portion through a lens 51. Similarly, projection units 53 and 54 are disposed behind the illumination window 44. The projection unit 53 is similar to the projection unit 46. The projection unit 54 is similar to the projection unit 47.

Figure 3:
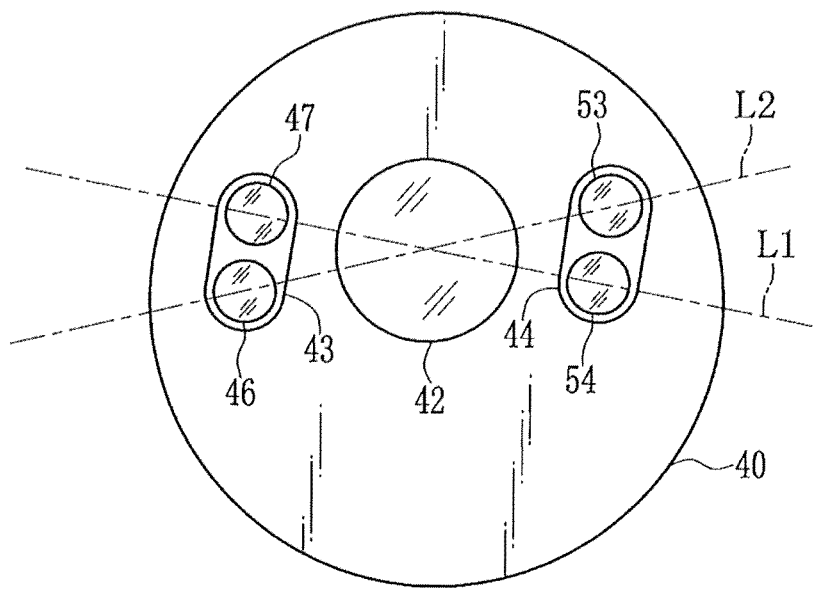
FIG. 3 is a front view of a distal portion.

As shown in FIG. 3, in the distal portion 40, the capture window 42 is disposed between the illumination windows 43 and 44. The four projection units 46, 47, 53, and 54 are arranged such that long and short dashed lines L1 between the output surfaces of the projection units 47 and 54 and long and short dashed lines L2 between the output surfaces of the projection units 46 and 53 cross each other at a center portion of the capture window 42. This arrangement prevents unevenness in illumination. Each of the projection units 47 and 54 is provided with the phosphor 50. The projection units 46 and 53 are not provided with the phosphor 50.

The plate-like phosphor 50 includes several kinds of fluorescent substances, for example, YAG fluorescent substances or BAM(BaMgAl$_{10}$O$_{17}$). These fluorescent substances absorb a part of the excitation light beams from the laser light source LD2 to emit green to yellow light (fluorescence). When the excitation light is applied to the phosphor 50, the green to yellow fluorescence emitted from the phosphor 50 and the excitation light passed through the phosphor 50 without being absorbed are combined to generate the white light (pseudo white light). A commercially available product under the product name Micro White (registered trademark) may be used as the phosphor.

Figure 4:
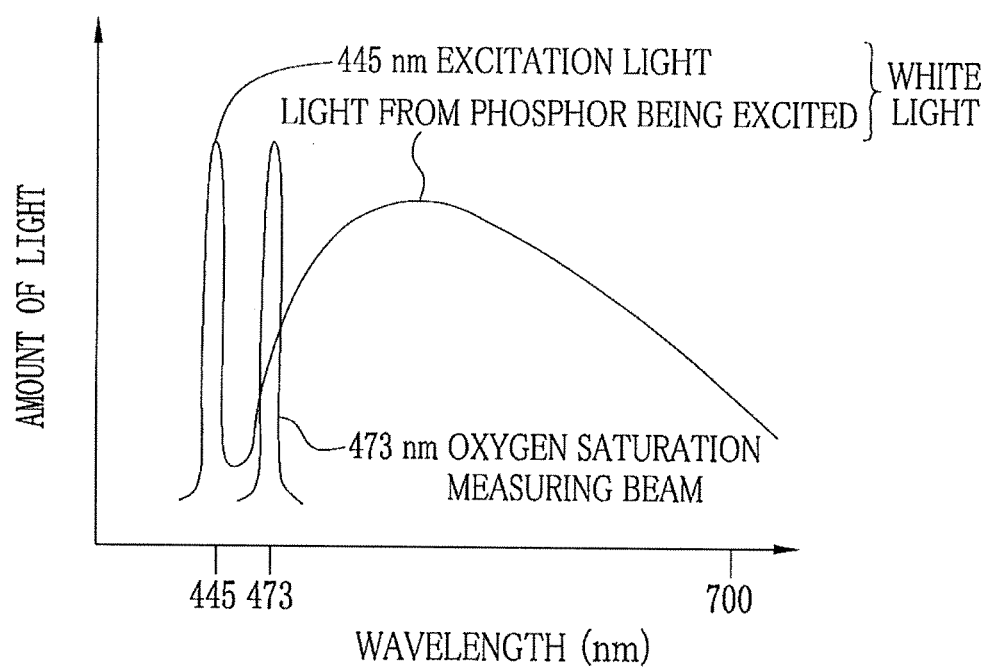
FIG. 4 is a graph showing emission spectra of oxygen saturation measuring beams and white light.

Accordingly, as shown in FIG. 4, the white light emitted from each of the projection units 47 and 54 (each having the phosphor 50) has an emission spectrum including a wavelength range of the excitation light having the center wavelength of 445 nm and a wavelength range approximately from 450 nm to 700 nm in which emission intensity of the fluorescence generated by the excitation light increases. On the other hand, the oxygen saturation measuring beams emitted from each of the projection units 46 and 53 (neither having phosphor 50) have an emission spectrum in a wavelength range around the center wavelength of 473 nm.

The white light of the present invention does not necessarily include all wavelength components of the visible light. Like the above pseudo white light, the white light only needs to include the light in a specific wavelength range such as the light of a primary color (red, green, or blue), for example. In other words, the white light may include the light having the wavelength components from green to red or the light having the wavelength components from blue to green, for example.

An objective lens unit (not shown) is provided behind the capture window 42. The objective lens unit takes in light (image light) reflected from the target portion of the subject. An image sensor 60 is provided behind the objective lens unit. The image sensor 60 is a CCD (Charge Coupled Device) or a CMOS (Complementary Metal-Oxide Semiconductor), for example. The image sensor 60 receives the image light of the target portion to generate an image thereof.

A light receiving surface (imaging surface) of the image sensor 60 receives the light from objective lens unit. Then, the image sensor 60 photoelectrically converts the light to output an imaging signal (analog signal). The image sensor 60 is a color CCD. On the light receiving surface, three kinds of pixels, R (red) pixels each provided with a red color filter, G (green) pixels each provided with a green color filter, and B (blue) pixels each provided with a blue color filter are arranged in a matrix with a predetermined pattern.

Figure 5:
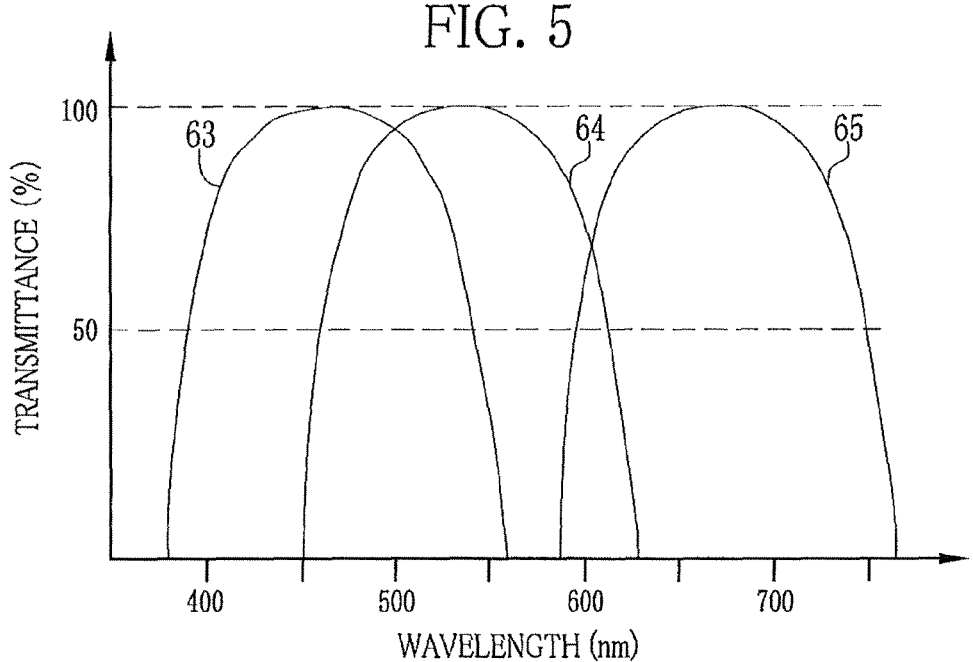
FIG. 5 is a graph showing spectral characteristics of R, G, and B color filters.

As shown in FIG. 5, the blue color filter has spectral characteristic 63. The green color filter has spectral characteristic 64. The red color filter has spectral characteristic 65. Accordingly, out of the light reflected from the target portion, the white light passes through all of the red, green, and blue color filters. Thereby, a color signal is outputted from each of the R, G, and B pixels of the image sensor 60. On the other hand, because the center wavelength of the oxygen saturation measuring beams is 473 nm, the color signal is outputted mainly from the B pixel.

A three-color signal, being the imaging signal (analog signal), outputted from the image sensor 60 is inputted to an A/D converter 68 through a scope cable 67. The A/D converter 68 converts the imaging signal (analog signal) into a binary image signal (digital signal) corresponding to a voltage level of the imaging signal. The image signal is inputted to an image processor 73 of the processor apparatus 13 through the connector section 36.

Figure 6A:
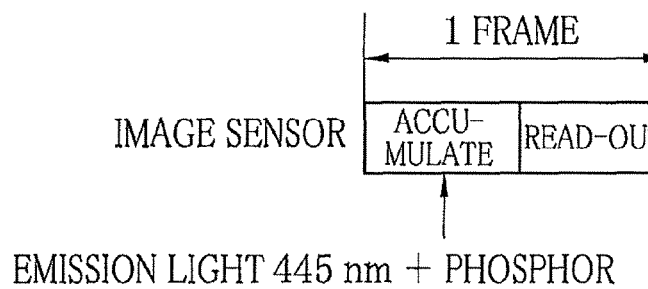
FIG. 6A is an explanatory view showing operation of an image sensor in a normal light mode.

An imaging controller 70 controls imaging of the image sensor 60. As shown in FIG. 6A, in the normal light mode, two steps, an accumulation step and a read-out step, are performed in a single frame period. In the accumulation step, electric charge obtained by the photoelectric conversion of the white light (445 nm+phosphor) is accumulated. In this embodiment, the white light (445 nm+phosphor) denotes that the white light is generated by applying the excitation light at 445 nm to the phosphor 50. In the read-out step, the electric charge accumulated is read out. The accumulation step and the read-out step are repeated alternately in the normal light mode.

Figure 6B:
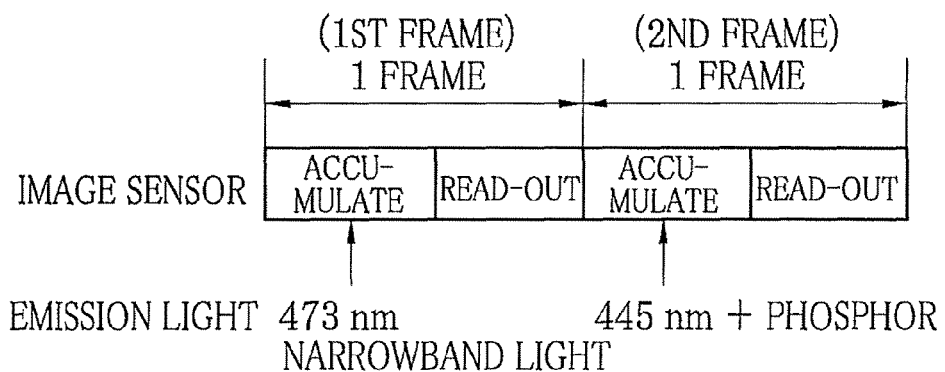
FIG. 6B is an explanatory view showing operation of the image sensor in an oxygen saturation mode.

On the other hand, in the oxygen saturation mode as shown in FIG. 6B, for the first frame, two steps, an accumulation step and a read-out step, are performed alternately in a single frame period. In the accumulation step, the electric charge obtained by photoelectric conversion of the oxygen saturation measuring beams (the narrowband light at 473 nm) is accumulated. In the read-out step, the electric charge accumulated is readout. Next, for the second frame, in the accumulation step, the electric charge obtained by photoelectric conversion of the white light (445 nm+phosphor) is accumulated. In the read-out step, the electric charge accumulated is read out. This imaging control using two frames is repeated in the oxygen saturation mode.

The image signal of the first frame is composed of a blue signal (B signal) B1 from the B pixel of the image sensor 60, a green signal (G signal) G1 from the G pixel of the image sensor 60, and a red signal (R signal) R1 from the R pixel of the image sensor 60. The image signal of the second frame is the same as the normal light image signal. The image signal of the second frame is composed of a B signal B2 from the B pixel, a G signal G2 from the G pixel, and an R signal R2 from the R pixel. The B signal B2 includes a signal corresponding to the light mainly composed of monochromatic excitation light having the center wavelength of 445 nm. This light also includes a small quantity of light with a blue component out of the white light emitted from the phosphor being excited. The G signal G2 includes a signal mainly corresponding to light in a wavelength range from 540 nm to 580 nm out of the white light emitted from the phosphor being excited. The R signal R2 includes a signal corresponding to light in a wavelength range from 590 to 700 out of the white light.

Inside the operation section 35 and the scope 32 of the endoscope apparatus 12, various channels (not shown) are provided. The channels include, for example, an air/water channel and a forceps channel through which a sample collecting device or the like is inserted.

The processor apparatus 13 is provided with a controller 72, the image processor 73, and storage 74. The controller 72 is connected to the display device 14 and the input device 15. The controller 72 controls operations of the image processor 73, the light source controller 20 of the light source apparatus 11, the imaging controller 70 of the endoscope apparatus 12, and the display device 14, according to a command instructing the observation mode and the like. The command is issued from the selection switch 17 or the input device 15 of the endoscope apparatus 12.

The image processor 73 is provided with a normal light image processing section 80 and an oxygen saturation image processing section 82. The image processor 73 performs predetermined image processing to the image signal from the endoscope apparatus 12. The normal light image processing section 80 performs predetermined image processing to the image signal to generate a normal light image.

The oxygen saturation image processing section 82 calculates information on the blood volume and the oxygen saturation of hemoglobin in blood of the target portion based on the image signal inputted from the endoscope apparatus 12. The oxygen saturation image processing section 82 generates an oxygen saturation image showing the oxygen saturation in pseudo color. The oxygen saturation image processing section 82 is provided with a signal ratio calculator 84, correlation storage 85, a blood volume and an oxygen saturation calculator 86, a reliability calculator 87, and an oxygen saturation image generator 88.

The signal ratio calculator 84 calculates a signal ratio between picture elements located at the same positions in the image signal of the first frame and the image signal of the second frame obtained in the oxygen saturation mode. The signal ratio(s) is calculated for every picture element or on a picture element by picture element basis in the image signal. In this embodiment, the signal ratio calculator 84 calculates a signal ratio B1/G2 between the B signal B1 of the first frame and the G signal G2 of the second frame, and a signal ratio R2/G2 between the R signal R2 of the second frame and the G signal G2 of the second frame. The signal ratios may be calculated only for the picture elements in a vascular portion of the image signals. In this case, the vascular portion is determined based on a difference between an image signal of the vascular portion and an image signal of a portion other than the vascular portion.

Figure 7:
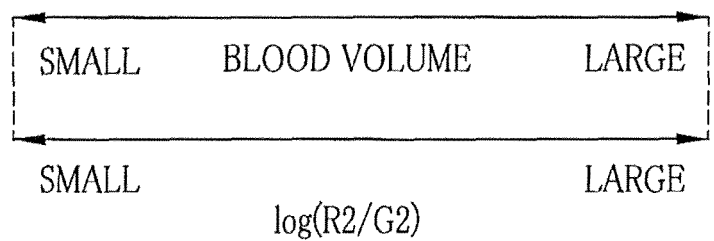
FIG. 7 is a graph showing a correlation between blood volume and a signal ratio R2/G2.

The correlation storage 85 stores a correlation between the blood volume and the signal ratio R2/G2, and a correlation between the oxygen saturation and the signal ratios B1/G2 and R2/G2. As shown in FIG. 7, the correlation between the blood volume and the signal ratio is stored in a one-dimensional table. The correlation is defined or determined such that the signal ratio R2/G2 increases with the blood volume. The signal ratio R2/G2 is stored in log scale.

Figure 8:
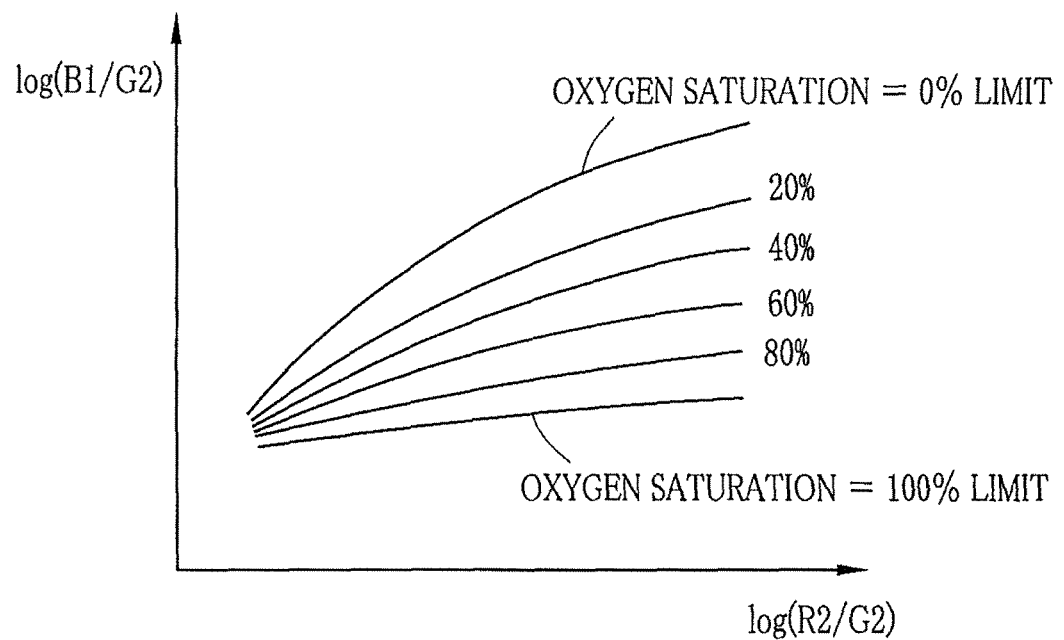
FIG. 8 is a graph showing a correlation between oxygen saturation and signal ratios B1/G2 and R2/G2.

On the other hand, as shown in FIG. 8, the correlation between the oxygen saturation and the signal ratios is stored in a two dimensional table. The two dimensional table defines contour lines of the oxygen saturation on a two dimensional space. The positions and shapes of the contour lines are obtained by physical simulation of light scattering, and vary according to the blood volume. For example, a space between the contour lines increases or decreases when there is a change in the blood volume. Here, the signal ratios B1/G2 and R2/G2 are stored in log scale.

Figure 9:
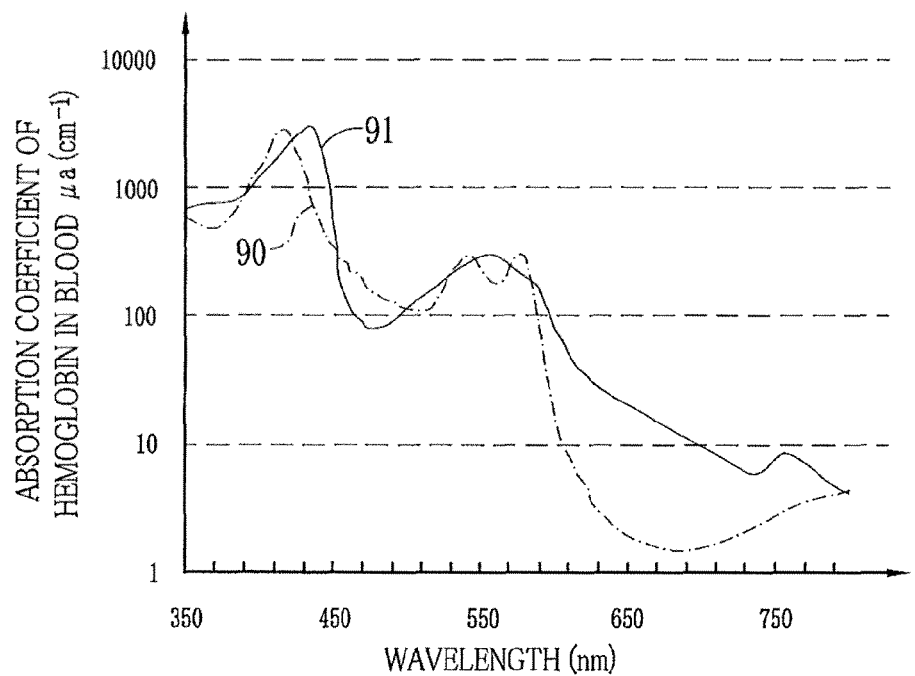
FIG. 9 is a graph showing absorption coefficients of hemoglobin.

The above-described correlations are closely related to light absorption property and light scattering property of oxyhemoglobin and deoxyhemoglobin shown in FIG. 9. In FIG. 9, a characteristic line 90 shows an absorption coefficient of oxyhemoglobin. A characteristic line 91 shows an absorption coefficient of deoxyhemoglobin. For example, as shown in FIG. 9, it is easy to obtain information on the oxygen saturation at 473 nm where a difference between the absorption coefficient of the oxyhemoglobin and the absorption coefficient of the deoxyhemoglobin is large. However, the B signal including a signal corresponding to the light at 473 nm is highly dependent on both the oxygen saturation and the blood volume. To obtain the oxygen saturation accurately without depending on the blood volume, the signal ratios B1/G2 and R2/G2 are used in addition to the B signal B1. The signal ratios B1/G2 and R2/G2 are obtained from the B signal B1, the R signal R2, and the G signal G2. The R signal R2 corresponds to the light which varies depending mainly on the blood volume. The G signal G2 is a reference signal for the B signal B1 and the R signal R2.

Based on wavelength dependence of the absorption coefficient of hemoglobin in blood, there are three important points.
1. In a wavelength range close to 470 nm, for example, in a blue wavelength range with the center wavelength of 470 nm±10 nm, the absorption coefficient varies significantly in accordance with a change in the oxygen saturation.
2. When averaged in a green wavelength range from 540 nm to 580 nm, the absorption coefficient is likely to be unaffected by the oxygen saturation.
3. In a red wavelength range from 590 nm to 700 nm, the absorption coefficient appears to vary significantly in accordance with a change in the oxygen saturation. Actually, however, the absorption coefficient is likely to be unaffected by the oxygen saturation because the value of the absorption coefficient is extremely small.

The blood volume and the oxygen saturation calculator 86 obtains both the blood volume and the oxygen saturation in each picture element using the correlations stored in the correlation storage 85 and the signal ratios B1/G2 and R2/G2 obtained by the signal ratio calculator 84. In the one-dimensional table in the correlation storage 85, the blood volume is a value corresponding to the signal ratio R2/G2. To obtain the oxygen saturation, as shown in FIG. 10, first, a point P corresponding to the signal ratios B1*/G2* and R2*/G2*, obtained by the signal ratio calculator 84, is determined in the two-dimensional space.

Figure 10:
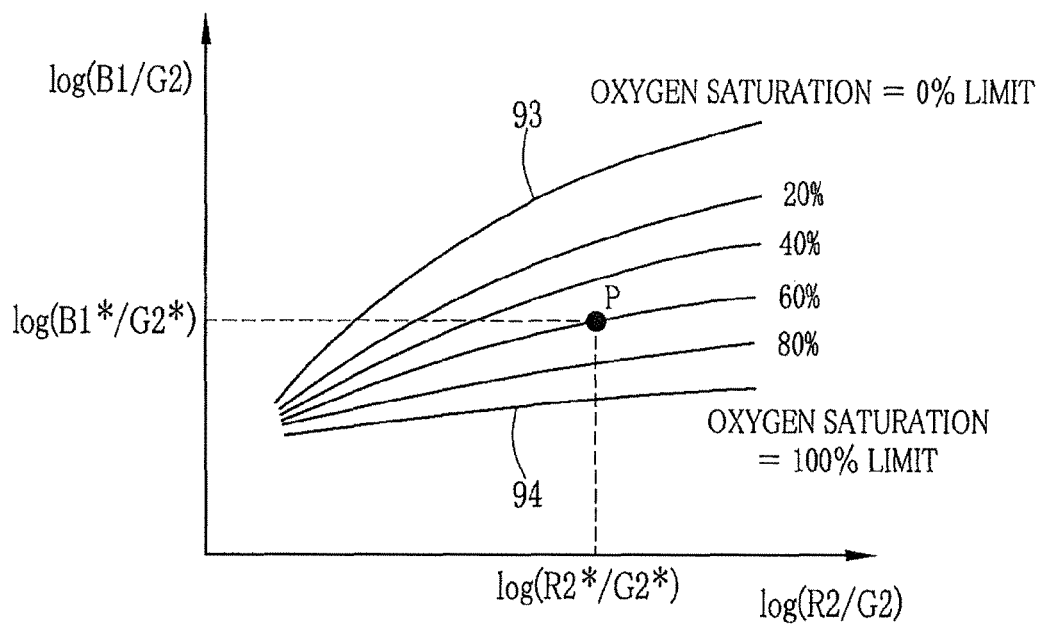
FIG. 10 is a graph describing how to determine the oxygen saturation from the signal ratios with the use of the graph of FIG. 8.

As shown in FIG. 10, when the point P is positioned between a lower limit line 93 (the oxygen saturation=0% limit) and an upper limit line 94 (the oxygen saturation=100% limit), the percentage of the oxygen saturation is the percentage expressed with the contour line where the point P is positioned. For example, in FIG. 10, the point P is positioned on the contour line of "60%", so the percentage of the oxygen saturation is 60%. If the point P is positioned outside of a range between the lower limit line 93 and the upper limit line 94, for example, when the point P is positioned above the lower limit line 93, the oxygen saturation is determined to be 0%. When the point P is positioned below the upper limit line 94, the oxygen saturation is determined to be 100%. Note that when the point P is positioned outside of a range between the lower limit line 93 and the upper limit line 94, reliability of the oxygen saturation in the picture element may be reduced so as not to display the oxygen saturation.

Figure 11:
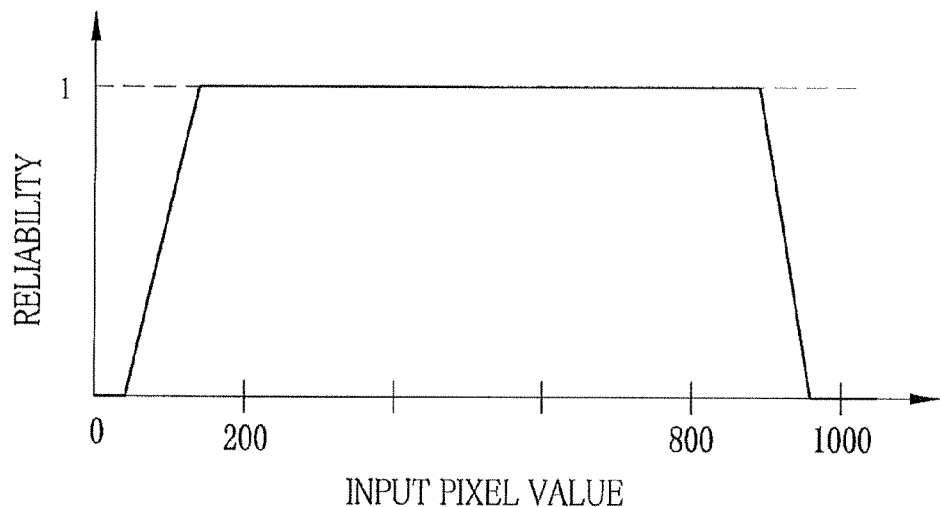
FIG. 11 is a graph showing a relation between the pixel value and reliability.

The reliability calculator 87 calculates the reliability in which accuracy of the oxygen saturation is quantified. In the first embodiment, the reliability is determined based on a pixel value of each of the B signal B1, the G signal G2, and the R signal R2 used for the calculation of oxygen saturation. The relation between the reliability and the pixel value of each signal is represented by a graph shown in FIG. 11. This relation is stored in a ROM 87a or the like. As shown in the graph, when the pixel value is within an appropriate range, the reliability is "1". On the other hand, the reliability is less than 1 and decreases gradually when the pixel value exceeds an upper limit and is extremely large, for example, when the electric charge is saturated due to the property of the image sensor. The reliability is also less than 1 and decreases gradually when the pixel value is less than a lower limit and is extremely small, for example, when S/N deteriorates.

The reliability is calculated for every picture element or on a picture element by picture element basis in the B signal B1, the G signal G2, and the R signal R2. Then, reliability Cp is calculated using the following expression. The reliability Cp refers to the reliability relative to each of the picture elements located at the same positions in respective B, G, and R signals.

$$Cp=Cp(B1) \times Cp(G2) \times Cp(R2)$$

Here, the Cp(B1) represents the reliability of the picture element of the B signal B1. The Cp(G2) represents the reliability of the picture element of the G signal G2. The Cp(R2) represents the reliability of the picture element of the R signal R2.

The oxygen saturation image generator 88 generates the oxygen saturation image showing blood vessel(s) in pseudo color corresponding to the oxygen saturation obtained by the blood volume and the oxygen saturation calculator 86. The oxygen saturation image is composed of a video signal. The video signal includes luminance Y and color difference signals Cb and Cr. The G signal G2 of the normal light image signal is assigned to the luminance Y. Each of the color signals Cb and Cr is determined in accordance with the oxygen saturation and the reliability. According to a color table 88a in which the oxygen saturation and the color difference signals are associated with each other, the color difference signals Cb and Cr, each corresponding to the oxygen saturation obtained by the blood volume and the oxygen saturation calculator 86, are determined.

Figure 12:
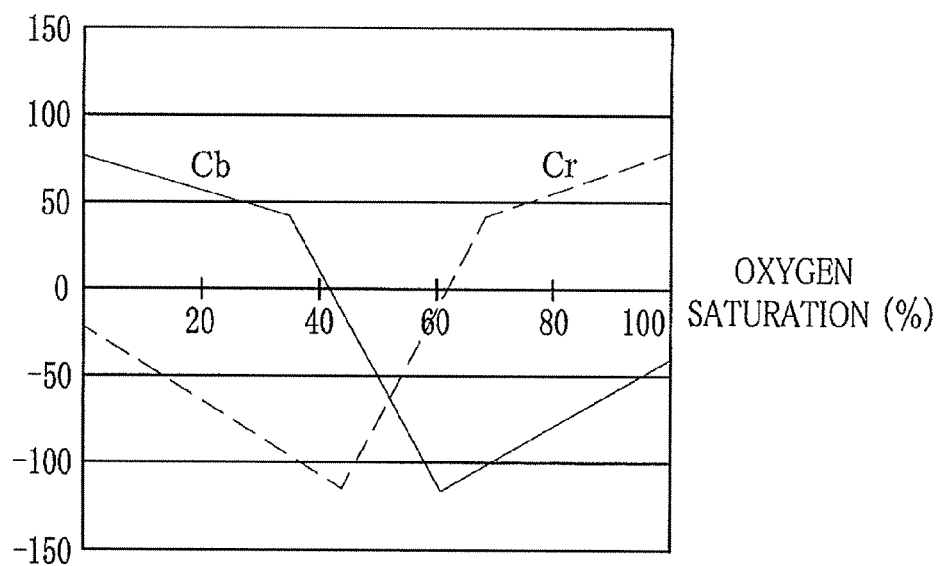
FIG. 12 is a graph showing a relation between the oxygen saturation and the color difference signals.

As shown in FIG. 12, in the color table 88a, when the oxygen saturation is high, a signal value of the color difference signal Cr is defined to be positive, while a signal value of the color difference signal Cb is defined to be negative. When the oxygen saturation is low, on the contrary, the signal value of the color difference signal Cr is defined to be negative, while the signal value of the color difference signal Cb is defined to be positive. When the oxygen saturation is at a medium level, a relation in magnitude between the signal value of the color difference signal Cr and the signal value of the color difference signal Cb reverses. Accordingly, as the oxygen saturation increases, the hue or color of the oxygen saturation image changes from blue to light blue to green to yellow to orange to red.

Next, as shown by the following two expressions, after the respective signal values of the color difference signals Cb and Cr are determined, the color difference signal Cb is multiplied by the reliability Cp to obtain a corrected color difference signal Cb'. The color difference signal Cr is multiplied by the reliability Cp to obtain a corrected color difference signal Cr'.

$$Cb'=Cb \times Cp$$

$$Cr'=Cr \times Cp$$

An oxygen saturation image composed of the corrected color difference signals Cb' and Cr' and the luminance Y is displayed on the display device 14. The above two expressions show that each of the corrected color difference signals approaches "0" in an area where the reliability Cp is low. An area of the oxygen saturation image with high reliability is displayed in pseudo color with high chroma, showing information on the oxygen saturation in a clear and distinguishable manner. On the other hand, in an area of the oxygen saturation image with low reliability, chroma of the area displayed on the display device 14 decreases as the reliability decreases, and thus the oxygen saturation image becomes monochromatic. This informs a user that the area has a small amount of information on the oxygen saturation.

Figure 13:
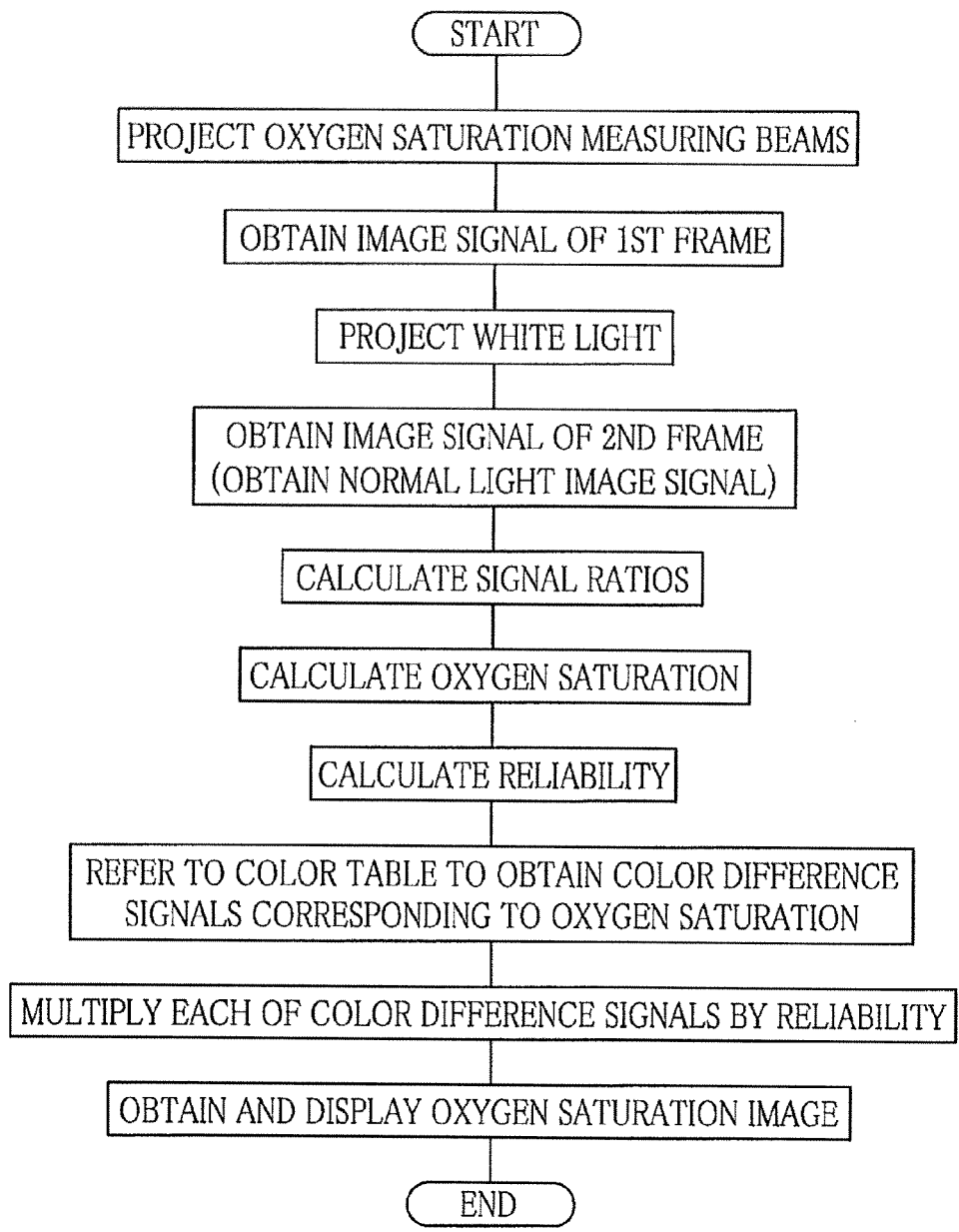
FIG. 13 shows a flowchart showing steps for generating an oxygen saturation image.
Figure 14:
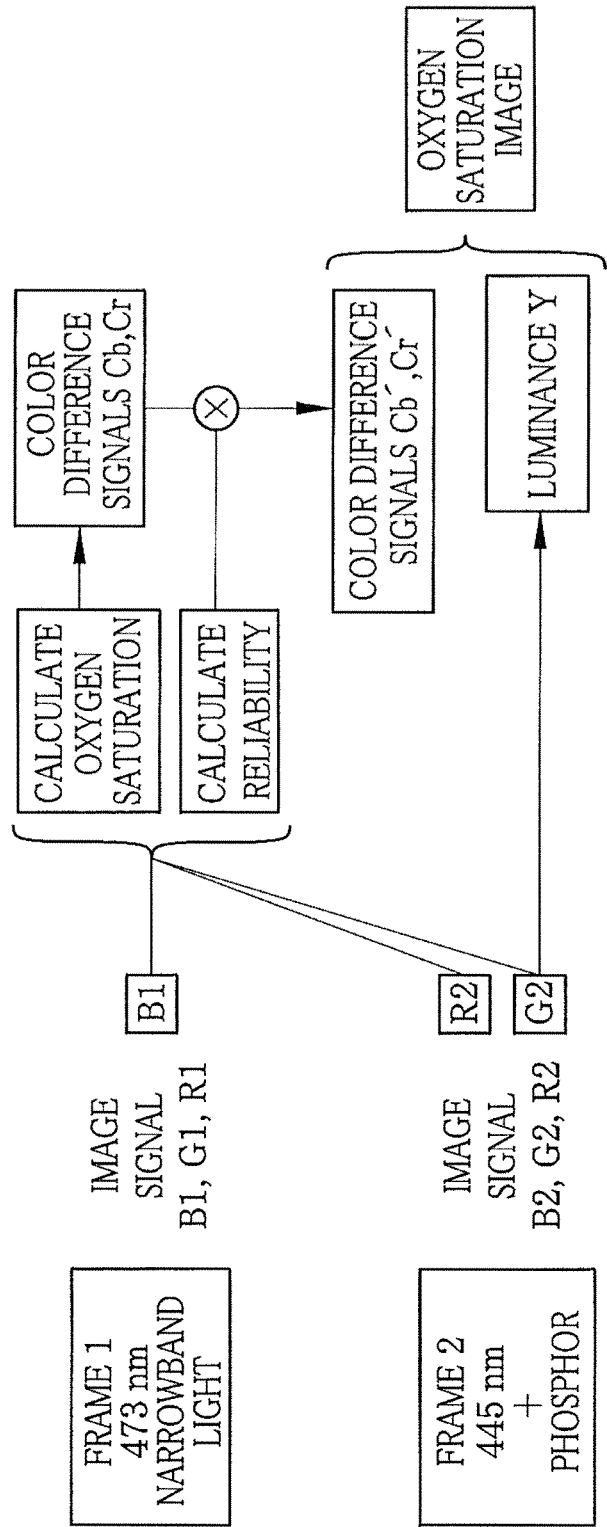
FIG. 14 is an explanatory view showing generation of the oxygen saturation image.

Next, the operation of the present invention is described with reference to FIGS. 13 and 14. When the observation mode is switched to the oxygen saturation mode using the selection switch 17 of the endoscope apparatus 12, the narrowband oxygen saturation measuring beams at the center wavelength of 473 nm are applied from the distal portion 40 to the target portion of the subject. The light reflected from the target portion is captured by the image sensor 60 being the color COD composed of B pixels, G pixels, and R pixels. Thereby, an image signal of a first frame is obtained. The image signal of the first frame is composed of a B signal B1, a G signal G1, and an R signal R1.

After the image signal of the first frame is obtained, the white light, generated by applying the excitation light at the center wavelength of 445 nm to the phosphor 50, is applied to the target portion of the subject through the distal portion 40. The image sensor 60 captures the light reflected from the target portion and the like. Thereby, an image signal (the normal light image signal) of a second frame is obtained. The image signal of the second frame is composed of a B signal B2, a G signal G2, and an R signal R2.

When the image signal of the second frame is obtained, the signal ratio calculator 84 obtains the signal ratios B1/G2 and R2/G2 between the picture elements located at the same positions in the image signal of the first frame and the image signal of the second frame. The signal ratios are obtained for every picture element or on a picture element by picture element basis. Thereafter, based on the correlation(s) stored in the correlation storage 85, the blood volume and the oxygen saturation calculator 86 obtains the oxygen saturation corresponding to the signal ratios B1/G2 and R2/G2. The oxygen saturation is obtained for every picture element or on a picture element by picture element basis. The reliability calculator 87 obtains the reliability Cp relative to each of the picture elements located at the same positions in the respective B signal B1, the G signal G2, and the R signal R2 used for the calculation of the oxygen saturation.

After the oxygen saturation and the reliability Cp are obtained for every picture element, the color table 88a in the oxygen saturation image generator 88 is referred to. Thereby, the color difference signals Cb and Cr, each corresponding to the oxygen saturation, are obtained from the color table 88a. The color difference signal Cb is multiplied by the reliability Cp to obtain the corrected color difference signal Cb'. The color difference signal Cr is multiplied by the reliability Cp to obtain the corrected color difference signal Cr'. The oxygen saturation image is generated from the corrected color difference signals Cb' and Cr', and the luminance Y. The G signal G2 of the normal light image signal is assigned to the luminance Y. The oxygen saturation image shows the blood vessel (s) in pseudo color varying in accordance with the oxygen saturation. The oxygen saturation image is displayed on the display device 14.

In a second embodiment of the present invention, the reliability is determined based on an amount of information on optical absorption spectrum of hemoglobin in blood, included in a pixel value of each of the B signal B1, the G signal G2, the R signal R2, and the B signal B2. The second embodiment is similar to the first embodiment except for the calculation of the reliability, so description other than that related to the calculation of the reliability is omitted.

When the pixel value of the B signal B1, the pixel value of the B signal B2, the pixel value of the G signal G2, and the pixel value of the R signal R2 are normalized by multiplying respective predetermined normalization constants so as to be proportional to reflectance, the following three relations described by expressions (M1) to (M3) hold true generally, in consideration of the optical absorption spectrum of hemoglobin.

(M1) B2<B1 (this relation may be reversed when the oxygen saturation and the blood volume are high)
(M2) B1>G2 (this relation may be reversed when the oxygen saturation is low and the blood volume is high.)
(M3) G2<R2

When opaque mucus is adhered to a surface of a mucosa, or when a residue exists, or when an artificial object or a pigment applied is captured in an image, the possibility to simultaneously satisfy the above three expressions becomes low.

Figure 15:
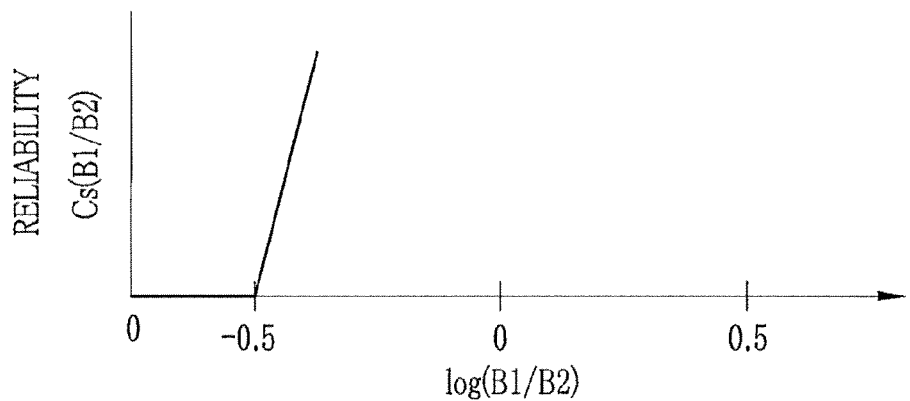
FIG. 15 is a graph showing a relation between a signal ratio B1/B2 and the reliability.
Figure 16:
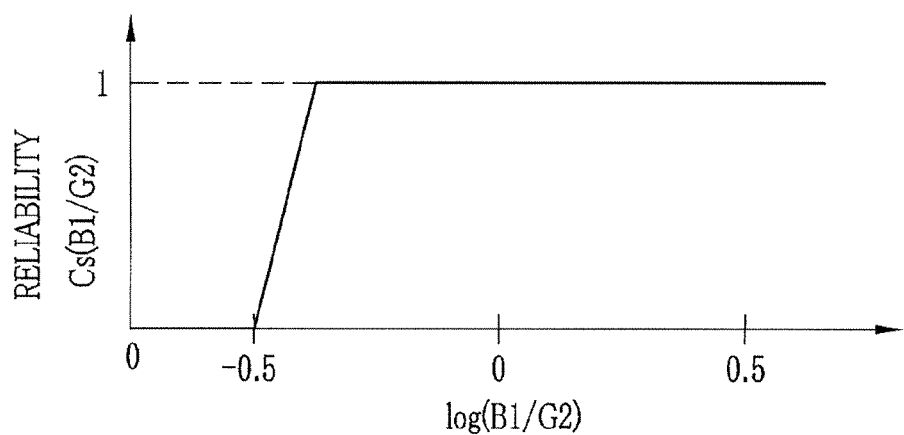
FIG. 16 is a graph showing a relation between a signal ratio B1/G2 and the reliability.
Figure 17:
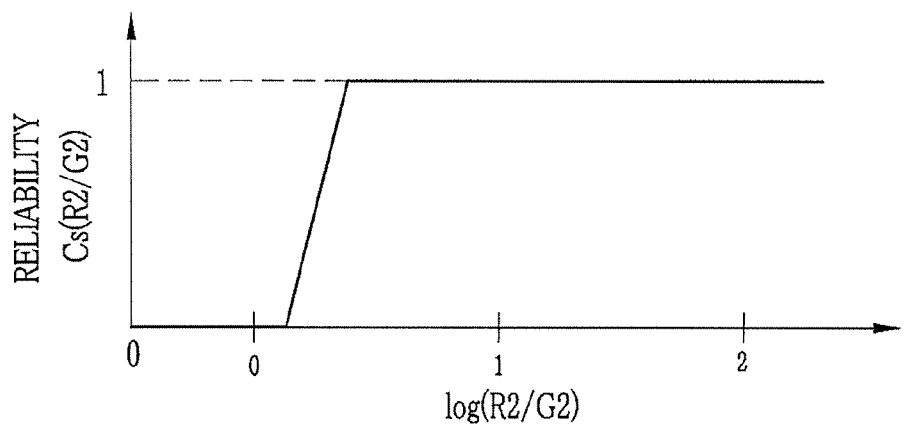
FIG. 17 is a graph showing a relation between a signal ratio R2/G2 and the reliability.

As shown in FIG. 15, when a signal ratio log(B1/B2) between the B signal B1 and the B signal B2 is greater than or equal to a predetermined value, the relation (M1) holds true, and the reliability Cs(B1/B2) is set to "1". When the signal ratio log(B1/B2) between the B signal B1 and the B signal B2 is less than the predetermined value, the reliability Cs(B1/B2) decreases gradually. As shown in FIGS. 16 and 17, when each of a signal ratio log(B1/G2) between the B signal B1 and the G signal 02 and a signal ratio log(R2/G2) between the R signal R2 and the G signal G2 is greater than or equal to a predetermined value, the relations (M2) and (M3) hold true. Thereby, each of the reliability Cs(B1/G2) and the reliability Cs(R2/G2) is set to "1". When each of the signal ratio log(B1/G2) and the signal ratio log(R2/G2) is less than the predetermined value, each of the reliability Cs(B1/G2) and the reliability Cs(R2/G2) decreases gradually. The relations between the reliability and each of the signal ratios shown in FIGS. 15 to 17 are stored in the ROM 87a.

As for expressions (M1) and (M2), the relation in magnitude may be reversed depending on the oxygen saturation and the blood volume. Accordingly, each of the reliability Cs(B1/B2) and the reliability Cs(B1/G2) does not start to decrease at a signal ratio "0" where respective pixel values are equal to each other. Instead, each of the reliability Cs(B1/B2) and the reliability Cs(B1/G2) decreases when the signal ratio is negative and away from "0" by a predetermined value. On the other hand, as for the expression (M3), there is a low possibility that the relation in magnitude reverses due to the oxygen saturation and the blood volume. Accordingly, the reliability Cp(R2/G2) decreases gradually as the positive signal ratio approaches "0".

After the reliability Cs(B1/B2) corresponding to the signal ratio log(B1/B2), the reliability Cs(B1/G2) corresponding to the signal ratio log(B1/G2), and the reliability Cs(R2/G2) corresponding to the signal ratio log(R2/G2) are obtained, the reliability Cs of each picture element is obtained using the following expression.

$$Cs=Cs(B1/G2) \times Cs(B1/G2) \times Cs(R2/G2)$$

Similar to the first embodiment, each of the color difference signals Cb and Cr is multiplied by the reliability Cs.

$$Cb'=Cb \times Cs$$

$$Cr'=Cr \times Cs$$

The oxygen saturation image is generated from the corrected color difference signals Cb' and Cr', and the luminance Y. The G signal G2 of the normal light image signal is assigned to the luminance Y. As shown by the following expressions, in addition to the reliability Cs described in this embodiment, each of the color difference signals Cb and Cr may be multiplied by the reliability Cp described in the first embodiment.

$$Cb'=Cb\times Cs\times Cp$$

$$Cr'=Cr\times Cs\times Cp$$

In a third embodiment of the present invention, the reliability is set in consideration of unevenness in distribution of the illumination light. When a difference in light distribution between the light from the projection units 47 and 54 (both with phosphor 50) and the light from the projection units 46 and 53 (neither with phosphor 50) is ignored, the unevenness in the light distribution increases from the center of the image toward the periphery thereof. The third embodiment is similar to the first embodiment except for the calculation of the reliability, so description other than that related to the calculation of the reliability is omitted.

The unevenness in the light distribution occurs because scattering characteristic of a scatterer in the phosphor 50, used for the illumination of the white light, varies depending on a wavelength and because light quantity distribution in an image varies slightly depending on a wavelength range due to aberration of the illumination optical system. The difference in the light quantity distribution becomes more apparent as becoming closer to the peripheral portion of the image. The difference in the light distribution also depends on unevenness of a surface of the subject, for example. Accordingly, when the oxygen saturation is calculated without correcting the difference in the light quantity distribution, the accuracy of the oxygen saturation calculated is likely to decline.

Figure 18:
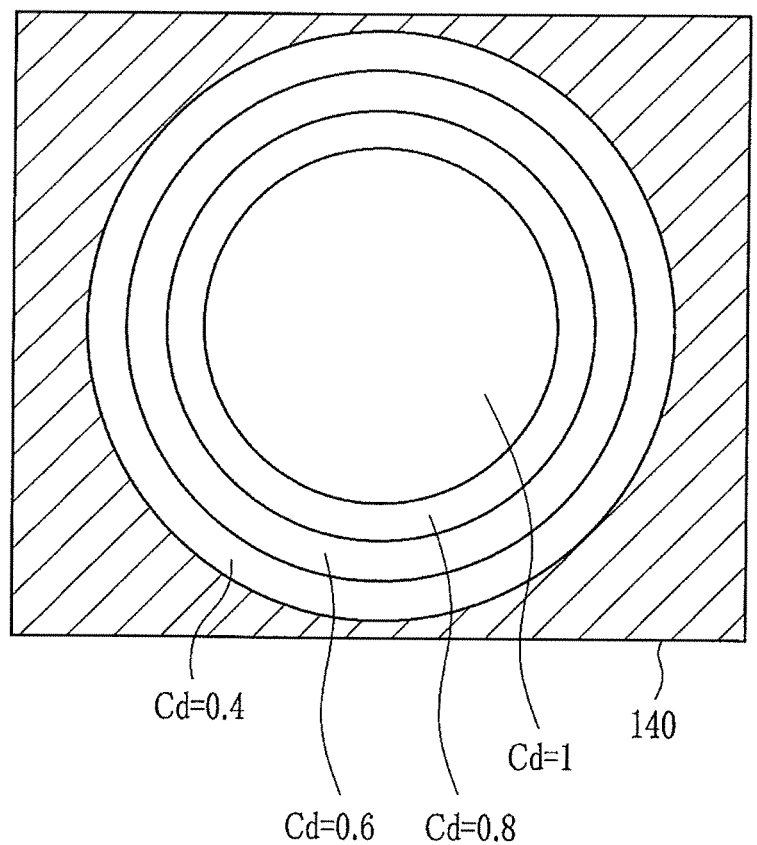
FIG. 18 is an explanatory view showing distribution of the reliability in which the reliability varies in accordance with a position in an image.

As shown in FIG. 18, the reliability Cd is distributed concentrically in an image 140. Namely, the reliability Cd is previously set such that the reliability Cd is high in a central area of the image, and gradually decreases from the central area to a peripheral area of the image 140. The reliability Cd is the lowest in an outermost peripheral portion of the image 140. Based on this reliability distribution, the reliability is determined for each of the picture elements of the image signal. The reliability is determined based on a region of the reliability distribution in which the picture element is located. The information on the reliability distribution shown in FIG. 18 is stored in the ROM 87a in the reliability calculator 87.

A method for calculating the reliability according to the third embodiment is not a dynamic method in which the reliability is calculated successively from the image signals obtained realtime as described in the first and second embodiments. Instead, the reliability is obtained from a predetermined reliability distribution set according to conditions such as a scattering characteristic of a scatterer in the phosphor and aberration of an illumination optical system. Here, the reliability is fixed once determined.

After the reliability Cd is obtained, on a picture element by picture element basis, from the reliability distribution shown in FIG. 18, each of the color difference signals Cb and Cr is multiplied by the reliability Cd, similar to the first embodiment. The corrected color difference signals Cb' and Cr' are obtained using the following expressions.

$$Cb'=Cb\times Cd$$

$$Cr'=Cr\times Cd$$

The oxygen saturation image is generated from the corrected color difference signals Cb' and Cr' and the luminance Y. The G signal G2 of the normal light image signal is assigned to the luminance Y. Note that each of the color difference signals Cb and Cr may be multiplied by at least one of the reliability Cp of the first embodiment and the reliability Cs of the second embodiment, in addition to the reliability Cd of the third embodiment.

$$Cb'=Cb\times Cd(\times Cp\times Cs)$$

$$Cr'=Cr\times Cd(\times Cp\times Cs)$$

Figure 19:
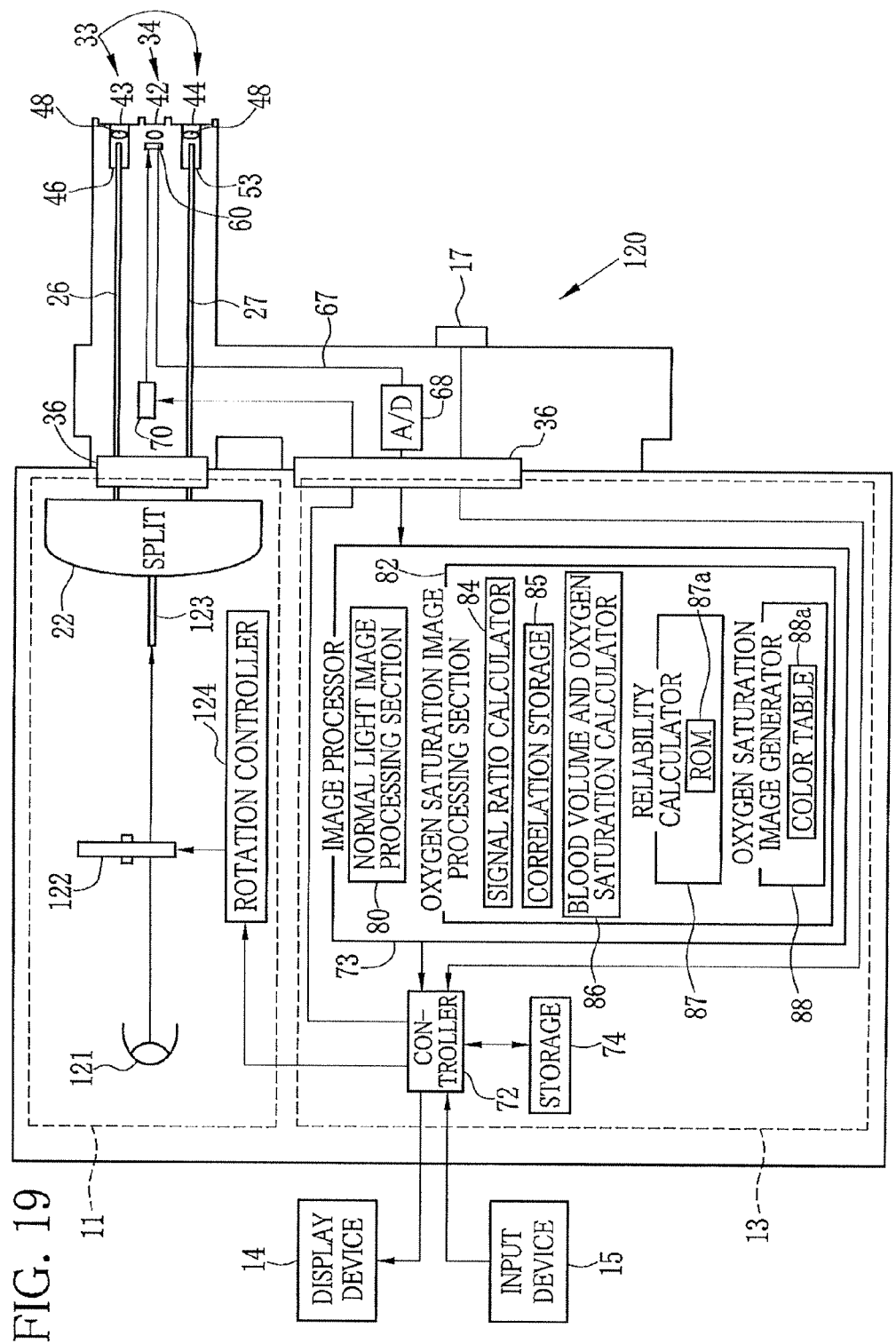
FIG. 19 is a block diagram of an endoscope system using a rotation filter in a light source apparatus.

In the above embodiments, the laser light sources LD1 and LD2 and the phosphor 50 are used to illuminate the target portion. Alternatively, as shown in FIG. 19, a rotating filter may be used to control the wavelength range of the illumination light. The endoscope system 120 is provided with a broadband light source 121, a rotating filter 122, an optical fiber 123, and a rotation controller 124. The broadband light source 121 is a xenon light source, for example, and emits white light having spectral intensity shown in FIG. 20. The rotating filter 122 allows the whole of the white light or a wavelength component corresponding to the oxygen saturation measuring beams out of the white light to pass therethrough. The light passed through the rotating filter 122 is incident on the optical fiber 123. The rotation controller 124 controls the rotation of the rotating filter 122. The light incident on the optical fiber 123 is split into two paths of light beams by the splitter 22. One of the two paths of the light beams is applied from the projection unit 46 to the target portion through the light guide 26. The other path of the light beams is applied from the projection unit 53 to the target portion through the light guide 27. For the parts other than the above, the endoscope system 120 has a similar configuration to the endoscope system 10, so description thereof is omitted.

Figure 21:
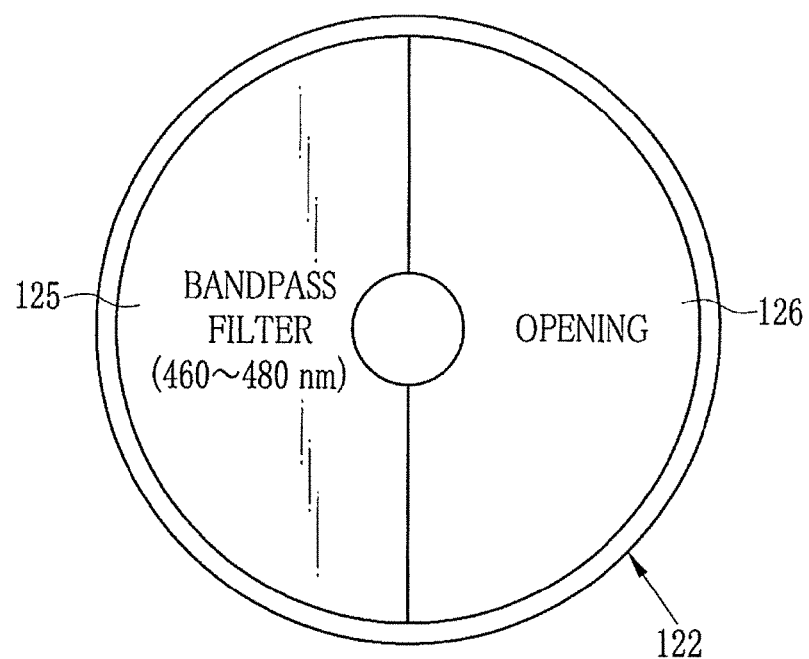
FIG. 21 is a front view of a rotating filter.

As shown in FIG. 21, the rotating filter 122 is provided with a bandpass filter 125 and an opening 126. Out of the white light, the bandpass filter 125 allows the oxygen saturation measuring beams (see FIG. 4) in the wavelength range from 460 nm to 480 nm to pass therethrough. The opening 126 allows the whole of the white light to pass therethrough. By rotating the rotating filter 122, the oxygen saturation measuring beams and the white light are applied alternately to the target portion. Similar to the above embodiments, the image signal of the first frame is obtained when the oxygen saturation measuring beams are applied. The image signal of the second frame is obtained when the white light is applied. The oxygen saturation image is generated from the two frames of the image signals in the similar manner to the above embodiments.

Figure 20:
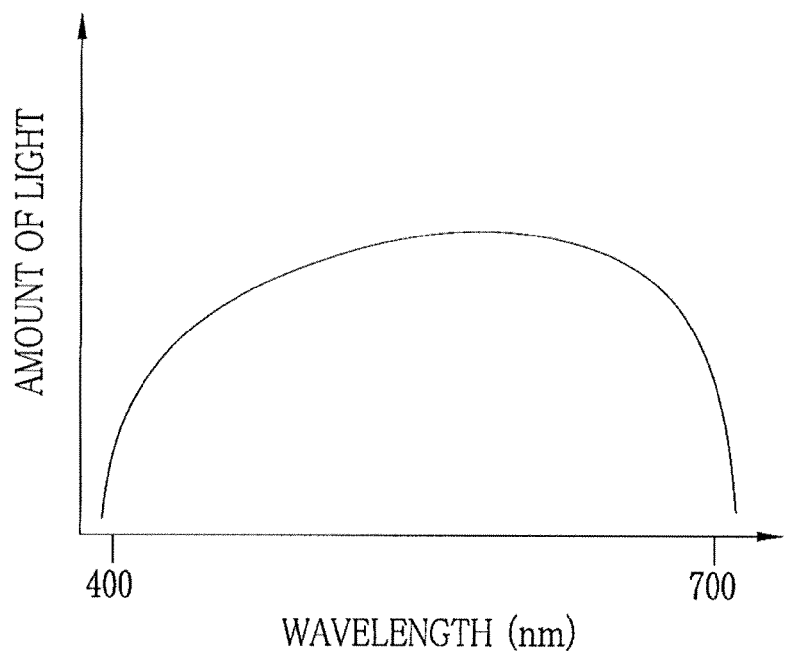
FIG. 20 is a graph showing an emission spectrum of white light.

Because the white light from the broadband light source 121 has the spectral intensity property shown in FIG. 20, the B signal B2 of the normal light image signal includes a signal of the light in the wavelength range from 400 nm to 530 nm. The G signal G2 includes a signal of the light in the wavelength range from 540 nm to 580 nm. The R signal R2 includes a signal of the light in the wavelength range from 590 nm to 700 nm. Methods for calculating the blood volume and the oxygen saturation are similar to those of the above embodiments, so the descriptions thereof are omitted.

Figure 22:
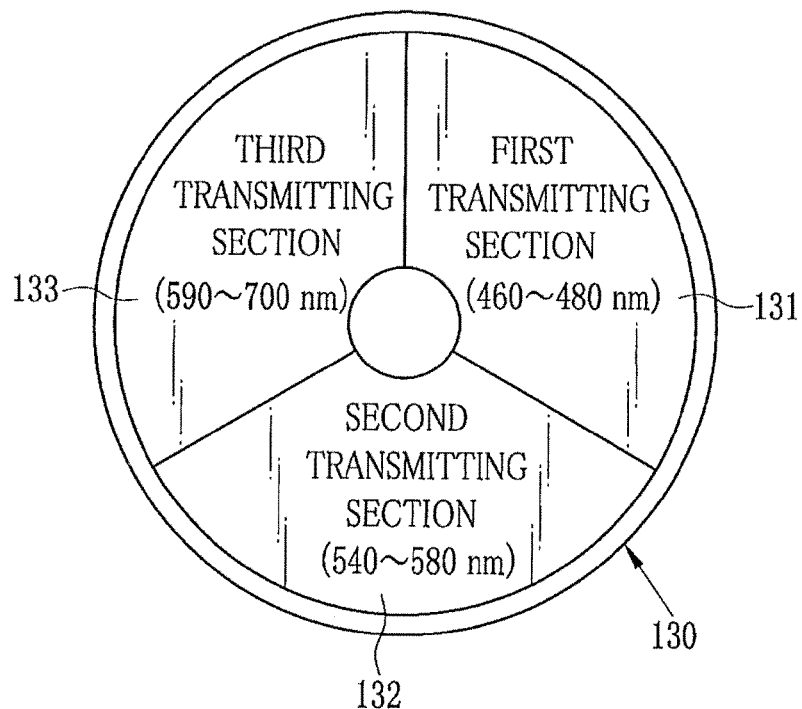
FIG. 22 is a front view of a rotating filter of another embodiment.

A rotating filter 130 shown in FIG. 22 may be used instead of the rotating filter 122 shown in FIG. 21. The rotating filter 130 is provided with first to third transmitting sections 131 to 133. Out of the white light from the broadband light source 121, the first transmitting section 131 allows first light beams to pass therethrough. The first light beams are in a wavelength range from 460 nm to 480 nm. Out of the white light, the second transmitting section 132 allows second light beams to pass therethrough. The second light beams are in a wavelength range from 540 nm to 580 nm. Out of the white light, the third transmitting section 133 allows third light beams to pass therethrough. The third light beams are in a wavelength range from 590 nm to 700 nm. When the rotating filter 130 is rotated, the first to third light beams are applied to the target portion sequentially and repeatedly.

When the rotating filter 130 is used, the monochrome image sensor 60 is used. The monochrome image sensor 60 performs three-color frame sequential imaging every time each of the first to third light beams is applied. By the applications of the first to third light beams, three frames of image signals are obtained, respectively. Out of the image signals, the image signal obtained when the first light beams are applied is defined as the B signal B. The image signal obtained when the second light beams are applied is defined as the G signal G. The image signal obtained when the third light beams are applied is defined as the R signal R.

Accordingly, the signal ratio R/G is used for the calculation of the blood volume. The signal ratios B/G and R/G are used for the calculation of the oxygen saturation. The signal ratio R/G corresponds to the signal ratio R2/G2 of the above embodiments. The signal ratio B/G corresponds to the signal ratio B1/G2 of the above embodiments. The methods for calculating the blood volume and the oxygen saturation are similar to those in the above embodiments, so descriptions thereof are omitted. To generate a pseudo-color blood volume image and the pseudo-color oxygen saturation image, the G signal G is assigned to the luminance.

Figure 23:
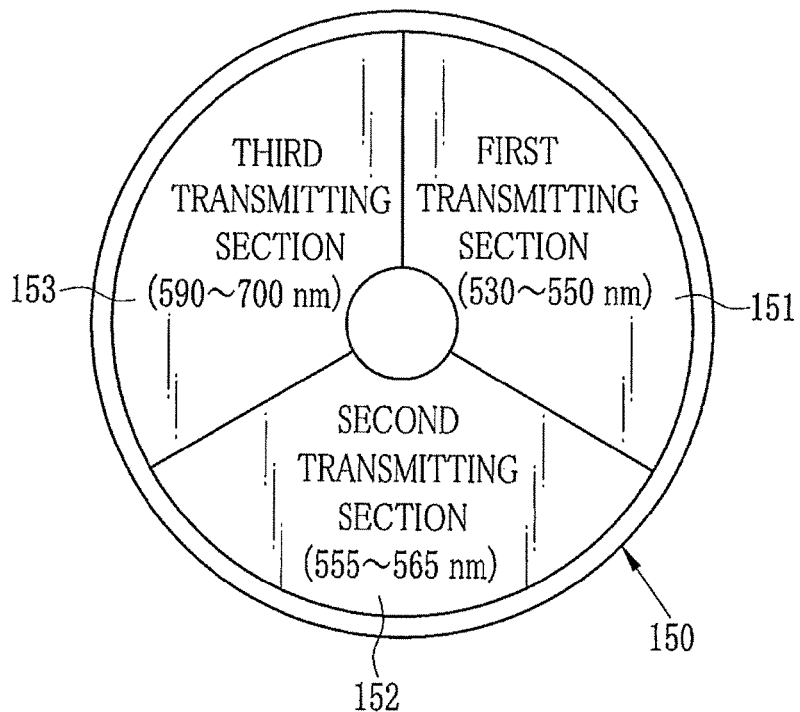
FIG. 23 is a front view of a rotating filter of further another embodiment.

Note that a rotating filter 150 shown in FIG. 23 may be used. The rotating filter 150 is provided with first to third transmitting sections 151 to 153. Out of the white light, the first transmitting section 151 of the rotating filter 150 allows first light beams to pass therethrough. The first light beams are in a wavelength range from 530 nm to 550 nm. Out of the white light, the second transmitting section 152 allows second light beams to pass therethrough. The second light beams are in a wavelength range from 555 nm to 565 nm. Out of the white light, the third transmitting section 153 allows third light beams to pass therethrough. The third light beams are in a wavelength range from 590 nm to 700 nm. When the rotating filter 150 is rotated, the first to third light beams are applied sequentially and repeatedly to the target portion.

When the rotating filter 150 is used, the color image sensor 60 captures an image every time each of the first to third light beams is applied. The first and second light beams are detected mainly by the G pixel of the image sensor 60. Accordingly, when the first and second light beams are applied, the G signals Ga and Gb are obtained as the image signals, respectively. On the other hand, the third light beams are detected mainly by the R pixel of the image sensor 60. Thereby, the R signal Rc is obtained as the image signal. Here, the image signals Ga and Rc are obtained from reflected light beams in respective wavelength ranges in each of which the absorption coefficient varies in accordance with a change in the oxygen saturation of hemoglobin in blood. The image signal Gb is obtained from the reflected light in a wavelength range in which the absorption coefficient is unchanged. Accordingly, the signal ratio Ga/Gb varies depending on the oxygen saturation and the blood volume. The signal ratio Rc/Gb varies depending mainly on the blood volume.

The signal ratio Rc/Gb is used for calculating the blood volume. The signal ratios Ga/Gb and Rc/Gb are used for calculating the oxygen saturation. The signal ratio Rc/Gb corresponds to the signal ratio R2/G2 of the above embodiments. The signal ratio Ga/Gb corresponds to the signal ratio B1/G2 of the above embodiments. The methods for calculating the blood volume and the oxygen saturation are similar to those in the above embodiments, so descriptions thereof are omitted. To generate the pseudo-color blood volume image and the pseudo-color oxygen saturation image, the G signal Ga or Gb is assigned to the luminance.

In the above embodiments, the oxygen saturation image is generated based on the oxygen saturation and reliability calculated using the blood volume and oxygen saturation calculator. The oxygen saturation image generated is displayed on the display device. Additionally, a blood volume image may be generated based on the blood volume and the reliability calculated using the blood volume and oxygen saturation calculator. The blood volume image generated may be displayed on the display device.

In the above embodiments, color tone information such as the color difference signals, associated with the oxygen saturation, is corrected or varied in accordance with the reliability. The oxygen saturation image is generated based on the corrected color difference signals. Alternatively or in addition, the amount of information on the oxygen saturation itself may be corrected or varied in accordance with the reliability. The oxygen saturation image maybe generated based on the corrected amount of information on the oxygen saturation.

Various changes and modifications are possible in the present invention and may be understood to be within the present invention.

What is claimed is:

1. An endoscope system comprising:
   an illuminating section for projecting illumination light to a portion to be observed, the portion including a blood vessel;
   an image signal obtaining section having an image sensor, the image signal obtaining section capturing reflection light reflected from the portion using the image sensor to obtain at least first to third image signals, the first image signal being obtained from first reflection light including a wavelength range in which an absorption coefficient varies in accordance with oxygen saturation of hemoglobin in blood, the second image signal being obtained from second reflection light including a wavelength range in which an absorption coefficient varies in accordance with blood volume, the third image signal being obtained from third reflection light including a wavelength range in which an absorption coefficient is unaffected by the oxygen saturation;
   an oxygen saturation calculator for obtaining oxygen saturation information while accounting for the blood volume on a picture element by picture element basis based on the first to third image signals;
   a reliability calculator for determining reliability of the oxygen saturation information on the picture element by picture element basis relative to at least one of the first to third image signals;
   an image processing section for generating an oxygen saturation image based on the oxygen saturation information and the reliability; and
   a display section for displaying the oxygen saturation image.

2. The endoscope system of claim 1, wherein the image processing section includes:
   a color tone information memory for storing a relation between the oxygen saturation information and color tone information; and
   an oxygen saturation image generator for correcting the color tone information with the reliability and generating the oxygen saturation image from corrected color tone information, and the color tone information is read out from the color tone information memory based on the oxygen saturation information.

3. The endoscope system of claim 1, wherein the reliability calculator determines the reliability in accordance with a pixel value of the picture element.

4. The endoscope system of claim 3, wherein the reliability decreases gradually when the pixel value exceeds an upper limit or when the pixel value is less than a lower limit.

5. The endoscope system of claim 1, wherein the reliability calculator determines the reliability based on a signal ratio between at least the two image signals and an optical absorption spectrum of the hemoglobin in blood.

6. The endoscope system of claim 1, wherein the reliability calculator determines the reliability in accordance with a position of the picture element.

7. The endoscope system of claim 6, wherein the reliability is highest when the picture element is located at a central area of an image, and the reliability decreases as the picture element is located closer to a peripheral area of the image.

8. The endoscope system of claim 2, wherein the color tone information comprises a signal value of a color difference signal.

9. The endoscope system of claim 1, wherein the image sensor comprises a color image sensor provided with R, G, and B color filters on an imaging surface, and white light is used as the illumination light to obtain the second and third image signals.

10. The endoscope system of claim 9, wherein the white light comprises pseudo white light generated by applying excitation light of a predetermined wavelength to a phosphor.

11. A processor apparatus used with an endoscope, the endoscope having an image signal obtaining section for obtaining at least first to third image signals from reflection light reflected from a portion to be observed, the portion including a blood vessel, the first image signal being obtained from first reflection light including a wavelength range in which an absorption coefficient varies in accordance with oxygen saturation of hemoglobin in blood, the second image signal being obtained from second reflection light including a wavelength range in which an absorption coefficient varies in accordance with blood volume, the third image signal being obtained from third reflection light including a wavelength range in which the absorption coefficient is unaffected by the oxygen saturation the processor apparatus including:
an oxygen saturation calculator for obtaining oxygen saturation information while accounting for the blood volume on a picture element by picture element basis based on the first to third image signals;
a reliability calculator for determining reliability of the oxygen saturation information on the picture element by picture element basis relative to at least one of the first to third image signals; and
an image processing section for generating an oxygen saturation image based on the oxygen saturation information and the reliability.

12. An image generating method comprising:
projecting illumination light to a portion to be observed, the portion including a blood vessel;
obtaining at least first to third image signals from reflection light reflected from the portion, the first image signal being obtained from first reflection light including a wavelength range in which an absorption coefficient varies in accordance with oxygen saturation of hemoglobin in blood, the second image signal being obtained from second reflection light including a wavelength range in which an absorption coefficient varies in accordance with blood volume, the third image signal being obtained from third reflection light including a wavelength range in which the absorption coefficient is unaffected by the oxygen saturation;
obtaining oxygen saturation information on a picture element by picture element basis based on the first to third image signals;
determining reliability of the oxygen saturation information while accounting for the blood volume on the picture element by picture element basis relative to at least one of the first to third image signals; and
generating an oxygen saturation image based on the oxygen saturation information and the reliability.

13. An endoscope system comprising:
an illuminating section for projecting illumination light to a portion to be observed, the portion including a blood vessel, the illumination light being pseudo white light generated by applying excitation light of a predetermined wavelength to a phosphor;
an image signal obtaining section having an image sensor, the image signal obtaining section capturing reflection light reflected from the portion using the image sensor to obtain at least first to third image signals, the first image signal being obtained from first reflection light including a wavelength range in which an absorption coefficient varies in accordance with oxygen saturation of hemoglobin in blood, the second image signal being obtained from second reflection light including a wavelength range in which an absorption coefficient varies in accordance with blood volume, the third image signal being obtained from third reflection light including a wavelength range in which the absorption coefficient is unaffected by the oxygen saturation;
an oxygen saturation calculator for obtaining oxygen saturation information while accounting for the blood volume on a picture element by picture element basis based on the first to third image signals;
a reliability calculator for determining reliability of the oxygen saturation information on the picture element by picture element basis relative to at least one of the first to third image signals;
an image processing section for generating an oxygen saturation image based on the oxygen saturation information and the reliability; and
a display section for displaying the oxygen saturation image.

14. The endoscope system of claim 13, wherein the reliability is highest when the picture element is located at a central area of an image, and the reliability decreases as the picture element is located closer to a peripheral area of the image.

15. The endoscope system of claim 3, wherein the reliability is reduced so as not to display the oxygen saturation image when the pixel value exceeds an upper limit or when the pixel value is less than a lower limit.

16. The endoscope system of claim 1, further comprising a correlation storage for storing a correlation between a signal ratio between at least the two image signals and the blood volume, and for storing a correlation between the signal ratio between at least the two image signals and the oxygen saturation.

* * * * *